United States Patent [19]

Rochester

[11] Patent Number: 4,997,276
[45] Date of Patent: Mar. 5, 1991

[54] APPARATUS AND METHOD FOR DETERMINING ELASTIC PROPERTIES OF OPTICAL FIBERS BY CONTACT AREA MEASUREMENT

[75] Inventor: James Rochester, Tucson, Ariz.

[73] Assignee: Hughes Aircraft Company, Los Angeles, Calif.

[21] Appl. No.: 454,229

[22] Filed: Nov. 3, 1989

[51] Int. Cl.⁵ ............................................. G01N 21/84
[52] U.S. Cl. ...................................... 356/73.1; 73/160
[58] Field of Search ........................... 356/73.1; 73/160

[56] References Cited

U.S. PATENT DOCUMENTS 4,940,891  7/1990  Rast ............................... 356/73.1 X Primary Examiner—Vincent P. McGraw
Attorney, Agent, or Firm—C. D. Brown; R. M. Heald; W. K. Denson-Low

[57] ABSTRACT

The elastic properties of an optical fiber (10) are determined from measurements of the contact area (20, 24) of the optical fiber (10) against a surface (16, 22), under a loading perpendicular to the surface. In a preferred approach, an optical fiber is passed over a curved surface (22) of a transparent lens in the form of a pulley (38), with a tension applied to the optical fiber (10). The buffer layer (14) of the optical fiber (10) is flattened against the curved contact surface (22), forming a contact region (24) whose area is measurable. The relative elastic deformability of the buffer layer (14), a function of its elastic modulus, is determined from the contact area and other measurable parameters. Contact area measurement is performed continuously as the optical fiber (10) is passed over the pulley (38) by monitoring the amount of light that is transmitted through the contact region (24). The variations in the elastic properties of the optical fiber (10) may therefore be measured continuously as the optical fiber (10) is transported over the pulley (38).

19 Claims, 2 Drawing Sheets

APPARATUS AND METHOD FOR DETERMINING ELASTIC PROPERTIES OF OPTICAL FIBERS BY CONTACT AREA MEASUREMENT

BACKGROUND OF THE INVENTION

This invention relates to an apparatus and method for determining the relative values of the properties of optical fibers, and, more particularly, to the continuous measurement of the variations in the elastic properties of the optical fiber buffer layer.

Optical fibers are strands of glass fiber processed so that light transmitted therethrough is subject to total internal reflection. A large fraction of the incident intensity of light directed into the fiber is received at the other end of the fiber, even though the fiber may be hundreds or thousands of meters long. Optical fibers have shown great promise in communications applications, because a high density of information may be carried along the fiber and because the quality of the signal is less subject to external interferences of various types than are electrical signals carried on metallic wires. Moreover, the glass fibers are light in weight and made from a highly plentiful substance, silicon dioxide.

Glass fibers are generally fabricated by preparing a preform of glasses of two different optical indices of refraction, one inside the other, and processing the preform to a fiber. The optical fiber is coated with a polymer layer termed a buffer to protect the glass from scratching or other damage. As an example of the dimensions, in a typical configuration the diameter of the glass optical fiber is about 125 micrometers, and the diameter of the fiber plus the polymer buffer is about 250 micrometers (approximately 0.010 inches).

The buffer layer is a cured polymer. In the preferred practice, a thin uniform layer of an acrylate monomer that is curable or polymerizable in ultraviolet (UV) light is coated onto the glass strand of the optical fiber. The coated optical fiber is passed through a curing station having ultraviolet light sources such as mercury lamps that produce ultraviolet light at 350 nanometers wavelength. Polymerization or curing is accomplished in about 1 second of exposure.

In one application, the finished optical fiber is wound onto a cylindrical or slightly tapered conical bobbin with many turns adjacent to each other in a side by side fashion. After one layer is complete, another layer of optical fiber is laid on top of the first layer, and so on. The final assembly of the bobbin and the wound layers of optical fiber is termed a canister, and the mass of wound fiber is termed the fiber pack. When the optical fiber is later to be used, the optical fiber is paid out from the canister in a direction parallel to the axis of the cylinder.

It has been demonstrated that the elastic properties of the buffer layer can play an important role in the winding and payout characteristics of the optical fiber. The elastic properties depend upon the thickness and degree of curing of the buffer polymer material. Thus, the ultimate operability of the optical fiber in some applications is dependent upon the success in producing a very uniformly applied and cured buffer layer. Because of this interrelationship, it has been found necessary to inspect the optical fiber and its buffer layer over its entire length, which may be thousands of meters, to ascertain the degree of cure of the polymer of the buffer layer and its elastic properties.

Until now, there has been no reliable procedure for testing the state of curing of the buffer continuously along the length of the optical fiber. At the present time, there exist only static axial loading procedures wherein a segment of the optical fiber is statically loaded in tension to determine its elastic properties, from which the properties of the buffer layer can be inferred. This approach is not sufficient to meet future demands for the testing of large amounts of optical fiber.

There exists a need for determining the elastic properties of optical fibers along their entire lengths, and in particular for the elastic properties of the buffer layer as a way of determining its cure state. The present invention fulfills this need, and further provides related advantages.

SUMMARY OF THE INVENTION

The present invention provides an apparatus and method for either statically or continuously testing the elastic properties of optical fibers, specifically the elastic properties of the buffer layer of the optical fiber. The approach permits the evaluation of the elastic properties of the buffer layer along the entire length of the optical fiber, in a continuous manner during fiber movement at rates of several meters per second. The relative elastic properties of the buffer layer along the length of the optical fiber are evaluated continuously as the optical fiber is passed through the apparatus.

In accordance with the invention, a process for evaluating an elastic deformation property of an optical fiber having a buffer layer comprises the steps of compressing an optical fiber against a contact surface to elastically deform the buffer layer against the contact surface; and measuring a contact area of the optical fiber against the contact surface. Once the contact area has been measured, it is then possible to compute an elastic deformation property of the optical fiber, if that information is required. In most instances, a relative measurement of properties is sufficient.

In another aspect of the invention, apparatus for evaluating an elastic deformation property of an optical fiber comprises means for forcing the optical fiber against a contact surface in a direction parallel to a diameter of the optical fiber; and means for measuring the contact area of the optical fiber against the contact surface. Again, a quantitative determination of the elastic property can be computed from the contact area.

The contact area of the optical fiber against the contact surface is a function of the elastic properties of the optical fiber, and most directly the elastic properties of the buffer layer. The more elastically deformable the buffer layer, the greater the contact area. The deformability of the buffer layer is in turn a function of the state of cure of the buffer layer. Generally, the more complete the cure, the greater the elastic modulus and the less deformable the buffer layer.

The contact area information derived from the testing procedure of the invention can be used in several different ways. The contact area can be used directly as a screening test. For example, if the contact area is greater than some preselected value, the state of cure is judged to be insufficient. The measured information thus gives a relative measure of elastic properties of the buffer layer. The contact area can also be used in conjunction with other measured data to compute quantitative values of the elastic properties.

The present approach is preferably implemented with the contact surface being a transparent lens in the form of a pulley. The optical fiber is passed over the pulley, and the contact area is found by measuring the amount of light that passes from the pulley/lens, through the contact surface, and into the optical fiber. The preferred light source is a laser whose beam is directed at the underside of the contact area through the body of the lens. Some fraction of the light is extracted through the contact area, and measured. The amount of light passed through the contact area is a measure of the contact area.

The approach of the invention permits the elastic property to be evaluated either continuously or statically. However, in view of the need to evaluate each segment of the entire length of long optical fibers, the continuous procedure is preferred. Other features and advantages of the invention will be apparent from the following more detailed description of the preferred embodiment, taken in conjunction with the accompanying drawings, which illustrate, by way of example, the principles of the invention.

DETAILED DESCRIPTION OF THE INVENTION

Figure 1:
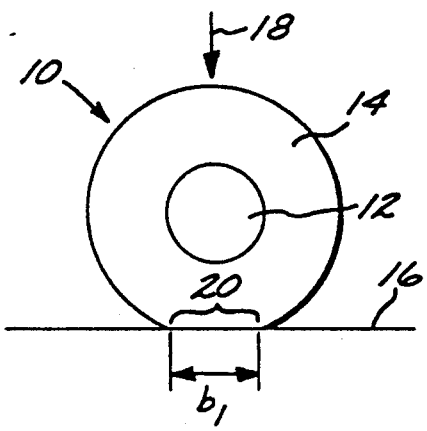
FIG. 1 is an end elevational view of an optical fiber transversely loaded against a contact surface.
Figure 2:
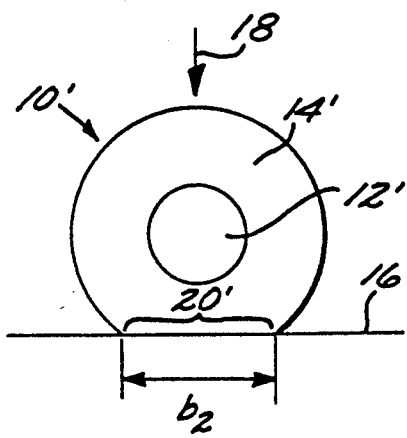
FIG. 2 is an end elevational view of another optical fiber transversely loaded against a contact surface.

As illustrated in FIGS. 1 and 2, an optical fiber 10 has a glass light conductor 12 and a buffer layer 14 surrounding the light conductor 12. The buffer layer 14 is a cured polymer, preferably an ultraviolet light cured acrylate polymer. Although a perfectly cured, uniform buffer layer 14 is the objective sought, manufacturing variations may result in imperfect curing or an irregularly thick layer 14 in some regions. The preferred embodiment of the present invention provides an approach for detecting such imperfect curing or irregularities in a continuous manner as the optical fiber 10 is transported past a sensor system.

FIGS. 1 and 2 illustrate a conceptual basis for the evaluation of the optical fiber 10. As shown in FIG. 1, an optical fiber 10 is pressed transversely to its length (that is, along a diameter) against a contact surface 16 with a force 18 that is sufficient to elastically deform the buffer layer 14. The force 18 is not so large that the buffer layer 14 may be permanently or plastically deformed. There is a contact region 20 that is flattened against the contact surface 16. The area of the contact region 20 is the length of the contact region 20 in the view of FIG. 1, $b_1$, times the dimension into the plane of the figure.

FIG. 2 illustrates a similar situation, except that the buffer layer 14' has not been fully cured, and is therefore softer than desired. Because the buffer layer 14' is soft, when the optical fiber 10' is pressed against the contact surface 16 with the same force 18, the size of the contact region 20' is larger, with an area of $b_2$ times the dimension into the plane of the figure.

The contact area of the contact region 20 (or, alternatively, the dimension b where the dimension into the plane of the figure is fixed) can thus be used as a basis for identifying those segments of the optical fiber 10 which have a buffer layer that is too compliant, and thence is undercured. A similar approach is used to identify any segments where the buffer layer is overcured, and the contact area is too small. The measurement of the contact area is therefore a basis for determining whether segments of the optical fiber have buffer layer properties not within an acceptable range of variation, and in one embodiment may be viewed as an acceptance test. Additionally, the value of the contact area can be used together with other information to reach quantitative measures of the elastic properties of the optical fiber, and, more particularly as to the preferred embodiment, the buffer layer.

The evaluation of the elastic deformation properties of the optical fiber can be accomplished against a flat contact surface 16 in the manner just described. However, for evaluating long lengths of optical fiber an alternative is preferred.

In accordance with a preferred aspect of the invention, a process for continuously evaluating an elastic deformation property of a buffer layer of an optical fiber comprises the steps of continuously passing the optical fiber over a curved contact surface while maintaining the optical fiber under tension; and measuring a contact area of the optical fiber against the contact surface.

Apparatus for evaluating an elastic compressional property of an optical fiber comprises a pulley having a cylindrical contact surface, an inner surface, and a transparent body; a light source system that directs a beam of light through the inner surface and the body of the pulley against the underside of the contact surface from within the pulley at an angle such that the light of the beam is reflected back into the body of the pulley; and a light collector that receives the portion of the light directed into the pulley from the light source system that is not reflected and passes out of the pulley through the contact surface. Preferably, the optical fiber has a buffer layer thereupon, and it is the elastic property of the buffer layer that is measured.

Figure 3:
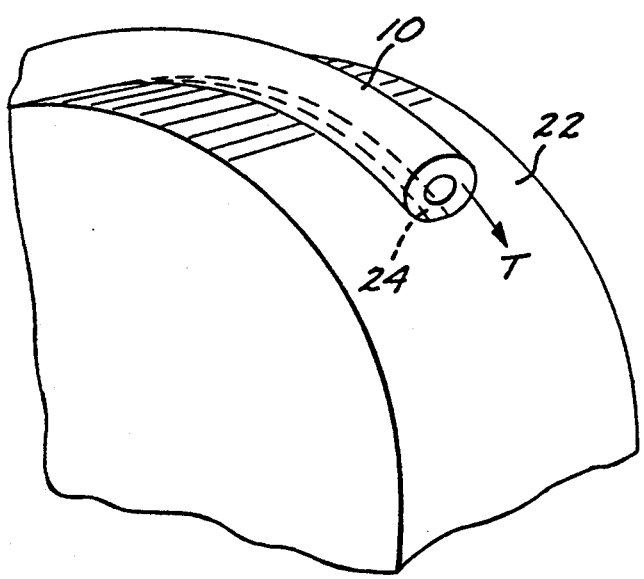
FIG. 3 is a perspective view of an optical fiber bent around a pulley.

FIG. 3 illustrates an optical fiber 10 that is deformed over a curved surface 22 under an applied tension T along the length of the optical fiber. The applied tension T produces a transverse component of force that presses the optical fiber 10 against the curved surface 22. There is a contact region 24 whose area varies with the properties of the buffer layer of the optical fiber in a manner generally similar to that described in relation to FIGS. 1 and 2. The deformation of the optical fiber 10 against the curved surface 22 has the advantage that the curved surface may be made part of a pulley that can be rotated around a shaft in a continuous manner, so that the optical fiber 10 can be continuously transported over the pulley and measured. A second advantage is that the transverse force is supplied as a component of the applied tension, which is normally present whenever an optical fiber is pulled over a pulley.

Figure 4:
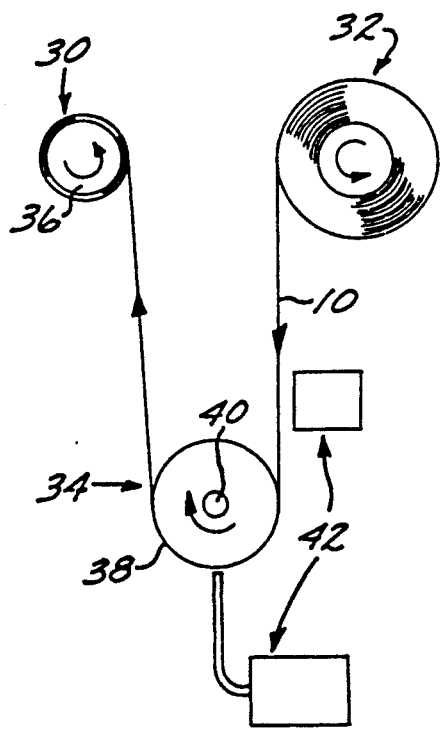
FIG. 4 is a schematic view of a system for evaluating the elastic properties of an optical fiber.

Using these principles, FIG. 4 illustrates in general aspects an apparatus 30 used to evaluate the elastic properties of an optical fiber 10 along its length by continuously transporting it through the apparatus 30. The optical fiber 10 is initially wound onto a supply spool 32. The optical fiber 10 is threaded through an evaluation apparatus 34, and thence to a takeup spool 36. The optical fiber 10 is continuously transported through the evaluation apparatus 34 by applying a rotation to the takeup spool 36, which draws the optical fiber 10 from the supply spool 32 and through the evaluation apparatus 34.

The evaluation apparatus 34 includes a pulley 38 rotatably mounted on a shaft 40, and around which the optical fiber 10 is passed, and a measurement head 42 that does not contact the optical fiber 10. The preferred construction of these elements will be discussed in relation to FIG. 6.

Figure 5:
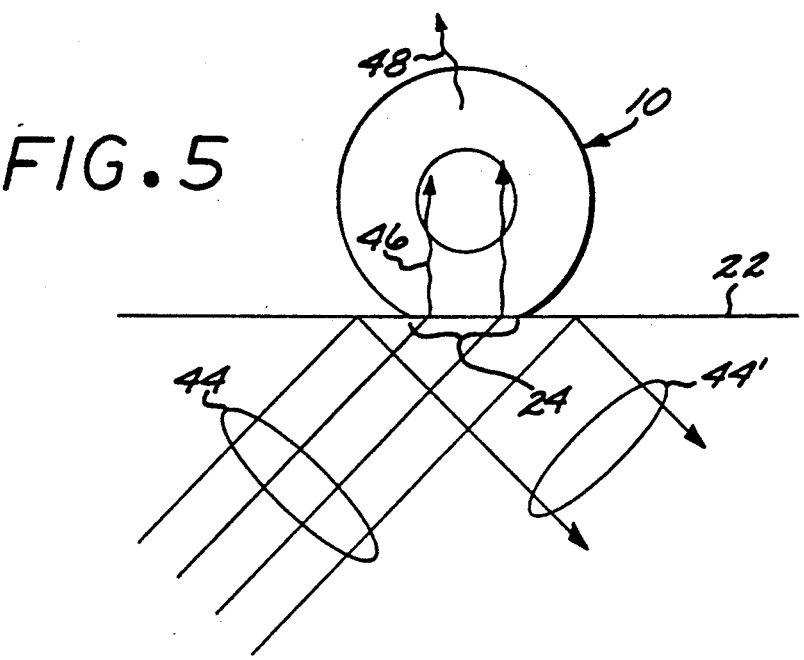
FIG. 5 is an end elevational view of an optical fiber transversely loaded against a transparent contact surface, illustrating the measurement of the contact area.

FIG. 5 illustrates the principle of measurement of the contact area as the optical fiber 10 is passed over the pulley 38, whose surface acts as the contact surface against which the optical fiber is pressed in the manner of FIG. 3. A uniform light beam 44 is directed against the underside of the curved contact surface 22. That is, the pulley 38 is made transparent to light, and the light beam is shone through the body of the pulley 38 and against the underside of the curved surface 22. The light beam 44 is directed against the underside of the curved surface 22 at such an angle that it would normally be totally internally reflected, in the absence of anything contacting the top side of the curved surface 22.

Where the optical fiber 10 contacts the curved surface 22 in the contact region 20, the reflecting behavior of the curved surface 22 is changed such that at least a portion of the light beam 44 incident upon the contact region 24 passes through the contact region 24 and is thereafter extracted from the body of the pulley 38. The extracted light rays are indicated diagrammatically by the rays 46. Some fraction of the extracted light rays will in turn escape from the optical fiber 10 as escaped light rays 48. The total intensity of either the extracted light rays 46 or the escaped light rays 48 is a measure of the area of the contact region 24. The greater the intensity, the larger the area of the contact region 20. Alternatively, the energy or intensity of the internally reflected light beam 44' could be measured, as its intensity decreases as the area of the contact region 24 increases.

Figure 6:
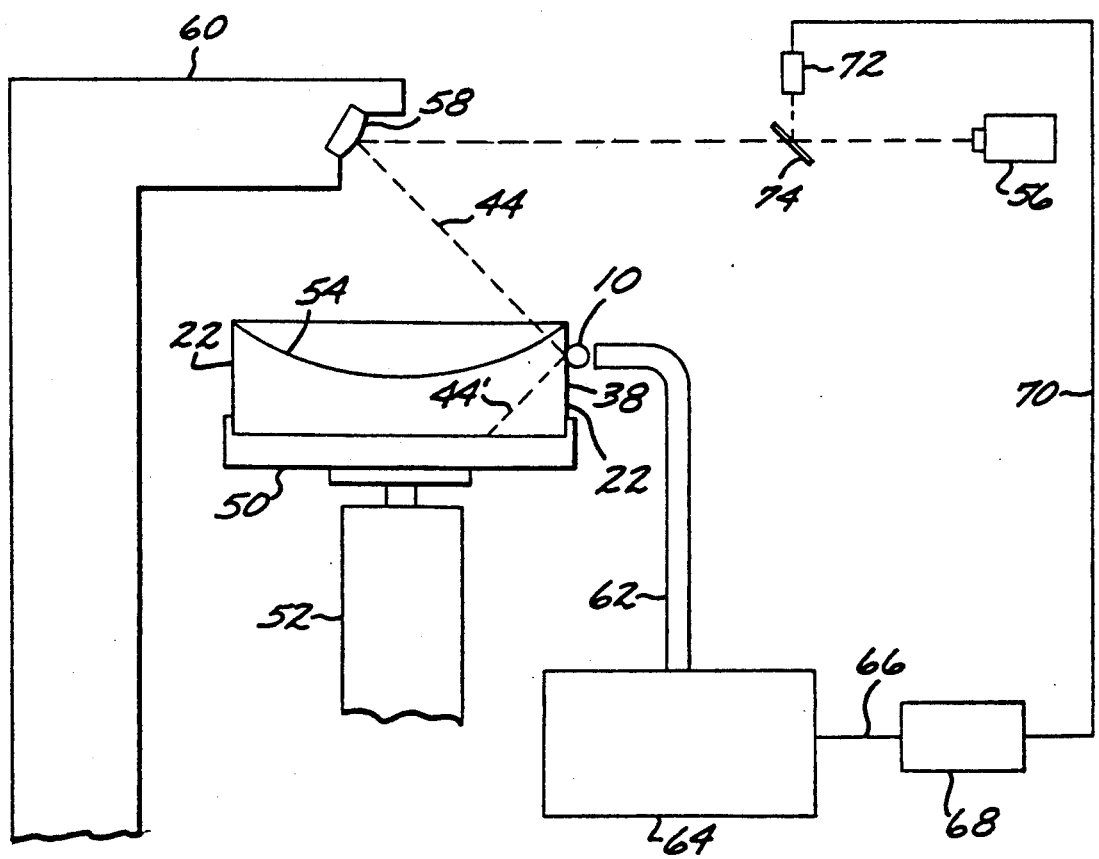
FIG. 6 is a schematic view of the preferred evaluation apparatus.

FIG. 6 illustrates a practical and preferred apparatus for continuously measuring the amount of escaped light rays 48 as the optical fiber 10 is passed over the transparent pulley 38. The pulley 38 is mounted on a support 50, which is mounted on a bearing 52 that permits the support 50 and the pulley 38 to turn freely. The optical fiber 10 is continuously transported over the pulley 38 in the direction out of the plane of the figure.

The pulley 38 is constructed as a transparent lens with a concavely curved inner surface 54. A light beam 44 is generated from a source 56 that is preferably a helium-neon laser that emits red light at a wavelength of 6328 Angstroms. The light beam 44 is reflected by a cylindrical mirror 58 mounted on a mirror mount 60 to enter the pulley 38 through the inner surface 54. The cylindrical mirror 58 spreads the beam 44 into a narrow fan in the dimension parallel to the plane of the figure. The fan intersects the cylinder in a line parallel to the cylindrical axis, providing uniformity of irradiation in the plane of varying contact. The effectiveness of the apparatus and the test would be less if the intensity of the beam 44 varies along the length of the fan.

The pulley 38 and its inner surface 54, and the mirror mount 60, are cooperatively arranged so that the light beam 44 strikes the inner surface 54 generally perpendicularly to that surface and passes into the body of the pulley 38. The components are further arranged such that the light beam 44 strikes the underside of the support surface 22 at an angle of approximately 45 degrees, as illustrated. This arrangement is readily attained in the manner illustsrated in FIG. 6. In the absence of the optical fiber 10, the light beam 44 is totally internally reflected from the underside of the curved surface 22.

A portion of the light of the beam 44 is extracted from the pulley through the contact region 20, some of which in turn escapes out of the optical fiber 10, in the manner discussed in relation to FIG. 5. The portion of the light that escapes from the optical fiber 10 is received and gathered by an fiber optic collector 62 and conducted to a laser light detector 64 where the intensity of the escaped light is measured.

An electrical signal 66 proportional to the intensity of the escaped light is provided to a computer 68. The signal 66 is proportional to the product of the contact length b times the width of the fan of the light beam 44. Since the width is constant, the signal 66 is proportional to the contact length b, which is the length of the contact region 20 or 24.

Additionally, a signal 70 proportional to the intensity of the beam 44 is measured by a laser light detector 72 that receives the light from a partially silvered mirror 74 in the beam 44, and is provided to the computer 68. The escaped light signal 66 is divided or normalized by the total beam signal 70 to account for variations in the output of the laser 56.

As discussed earlier, the magnitude of the escaped light signal 66 is a direct measure of the contact area of the contact region 20. This signal 66 can be compared against preselected acceptability criteria to determine whether the segment of the optical fiber 10 being measured at that time meets the acceptability criteria. For example, if the preselected acceptability criteria require that the normalized signal produced by dividing the signal 66 by the signal 70 be within a preselected range, and the normalized signal is within that range, then the properties of the buffer layer 14 are determined to be within the proper acceptable range. On the other hand, if the normalized signal is not within that preselected acceptability range, an error condition requiring further investigation is indicated.

The signal 66 can also be used in conjunction with other information to provide a quantitative measure of the elastic properties of the buffer layer 14. For example, a mathematical analysis of the contact length b for an optical fiber 10 having a buffer layer 14 yields the approximate expression $$E = DT/Rb^2$$

where E is the elastic compressional modulus, D is the diameter of the optical fiber, T is the applied tension, and R is the radius of the pulley. The value of b is obtained from the electrical signal 66 and a calibration of that signal against true contact area that is obtained during the initial calibration of the apparatus. The computer 68 can perform this calculation at the same time that the relationship of the electrical signal 66 to the acceptability is determined. Other elastic properties can be calculated, as needed.

The buffer layer is in fact viscoelastic to some degree, and the term "elastic" as used herein is intended to encompass both time-independent elastic deformation and time-dependent viscoelastic deformation. Because of the viscoelastic nature of the deformation, a calculational approach such as that presented in relation to the above equation is meaningful only if the optical fiber is transported over the pulley at a constant speed, and thence deformation rate. The same is true for qualitative analyses such as the acceptance test discussed previously.

The present invention thus provides an apparatus and method for the measurement of the elastic properties of the buffer layer of an optical fiber on a continuous basis as the optical fiber is transported over the pulley of the measurement system. The measurement can be continuously made at speeds as high as several meters per second. Although particular embodiments of the invention have been described in detail for purposes of illustration, various modifications may be made without departing from the spirit and scope of the invention. Accordingly, the invention is not to be limited except as by the appended claims.

What is claimed is:

1. A process for evaluating an elastic deformation property of an optical fiber having a buffer layer, comprising the steps of:
   compressing an optical fiber against a contact surface to elastically deform the buffer layer against the contact surface; and
   measuring a contact area of the optical fiber against the contact surface.

2. The process of claim 1, including the additional step, after the step of measuring, of
   computing an elastic deformation property of the optical fiber.

3. The process of claim 1, wherein the elastic deformation property is related to the elastic compressional modulus of the buffer layer.

4. The process of claim 1, wherein the step of compressing is accomplished by applying a load in a direction parallel to a diameter of the optical fiber.

5. The process of claim 1, wherein the contact surface is curved, and the step of compressing is accomplished by applying tension to the optical fiber.

6. The process of claim 1, wherein the contact surface is transparent to light, and the step of measuring includes the step of directing a beam of light through the contact surface toward the contact area.

7. The process of claim 1, wherein the contact surface is an outer surface of a transparent pulley whose outer surface is cylindrical, and which further has an inner surface that is a lens.

8. The process of claim 7, wherein the step of measuring includes the steps of
   passing a beam of light through the inner surface and the body of the transparent pulley, and
   collecting the light that passes through the contact area of the contact surface.

9. A process for continuously evaluating an elastic deformation property of a buffer layer of an optical fiber, comprising the steps of:
   continuously passing the optical fiber over a curved contact surface while maintaining the optical fiber under tension; and
   measuring a contact area of the optical fiber against the contact surface.

10. The process of claim 9, including the additional step, after the step of measuring, of
    computing an elastic deformation property of the optical fiber.

11. The process of claim 9, wherein the support is a pulley.

12. The process of claim 11, wherein the pulley includes a negative lens.

13. The process of claim 9, wherein the contact surface is transparent, and the step of measuring is performed by directing a beam of light through the contact surface against the contact area of the optical fiber and collecting the light passing through the contact area.

14. The process of claim 10, wherein the elastic deformation property is related to the elastic compressional modulus under constant transport speed.

15. Apparatus for evaluating an elastic deformation property of an optical fiber, comprising:
    means for forcing the optical fiber against a contact surface in a direction parallel to a diameter of the optical fiber; and
    means for measuring the contact area of the optical fiber against the contact surface.

16. The apparatus of claim 15, wherein the optical fiber has a buffer layer, and the elastic property of the buffer layer is measured.

17. The apparatus of claim 15, further including
    means for evaluating the elastic deformation of the buffer layer from the measurement of the contact area of the optical fiber against the contact surface.

18. Apparatus for evaluating an elastic compressional property layer of an optical fiber, comprising:
    a pulley having a cylindrical contact surface, an inner surface, and a transparent body;
    a light source system that directs a beam of light through the inner surface and the body of the pulley against the underside of the contact surface from within the pulley at an angle such that the light of the beam is reflected back into the body of the pulley; and
    a light collector that receives the portion of the light directed into the pulley from the light source system that is not reflected and passes out of the pulley through the contact surface.

19. The apparatus of claim 18, wherein the optical fiber has a buffer layer, and the elastic property of the buffer layer is measured.

* * * * *